United States Patent [19]

Gibbons

[11] 4,075,001
[45] Feb. 21, 1978

[54] 3-AMINOISOTHIAZOLE DERIVATIVES AS HERBICIDES

[75] Inventor: Loren Kenneth Gibbons, Medina, N.Y.

[73] Assignee: FMC Corporation, Philadelphia, Pa.

[21] Appl. No.: 697,449

[22] Filed: June 18, 1976

[51] Int. Cl.$^2$ ............... C07D 275/02; A01N 9/12
[52] U.S. Cl. .............................. 71/90; 260/306.8 A
[58] Field of Search .................. 260/306.8 A; 71/90

[56] References Cited
U.S. PATENT DOCUMENTS 3,816,420   6/1974   Gibbons et al. ............ 260/306.8 A

FOREIGN PATENT DOCUMENTS 6,704,895   10/1967   Netherlands ............... 260/306.8 A Primary Examiner—Richard J. Gallagher
Attorney, Agent, or Firm—Harrison H. Young, Jr.; Henry R. Ertelt

[57] ABSTRACT

A new class of herbicidal compounds consisting of 1-alkyl- and 1,1-dialkyl-3-(4-substituted-3-amino-5-isothiazolyl)ureas and N-(4-substituted-3-amino-5-isothiazolyl)-alkanamides, in which the 4-substituent consists of cyano and carbamoyl, exhibits preemergence and postemergence herbicidal activity, controlling effectively the growth of a wide spectrum of grassy and broad-leaved plant species. The synthesis of members of this class is described in detail, and the utility of representative compounds is exemplified.

17 Claims, No Drawings

3-AMINOISOTHIAZOLE DERIVATIVES AS HERBICIDES

This invention describes novel herbicidal compounds, new herbicidal compositions, and new methods for preventing and destroying undesired plant growth by preemergence and postemergence application of said new and useful herbicidal compositions to the locus where control is desired. Effective control of the growth of a variety of grassy and broad-leaved plant species is obtained. At herbicidally effective levels of application, some compounds of the invention show selectivity favorable to corn, sorghum and related species. The herbicidal compositions may be applied and utilized by commonly accepted methods.

Herbicidal isothiazole compounds having an alkyl group on the 3-position of the isothiazole ring; a cyano, carboxamide or alkoxycarbonyl group on the 4-position; and a substituted urea on the 5-position have been described in the patent literature. See, for example, Belgian Pat. No. 817,903 and published French application No. 2,132,191. It has now been found that excellent herbicidal activity is obtained by having present on the 3-position, instead of an alkyl group, a secondary or tertiary amino group. It has also been found that herbicidal activity is obtained with compounds having such a 3-amino group, when the compound has in the 5-position, instead of a substituted urea group, a substituted alkanoylamino group. Thus, in one aspect of the invention, novel herbicidal compounds contain an isothiazole ring having the following classes of substituents: on the 3-position, a secondary or tertiary amino group; on the 4-position, a cyano, carboxamide or alkoxycarbonyl group; and on the 5-position, a substituted urea or alkanoylamino group.

One group of herbicidal compounds in accordance with this invention has the following structure (on which the numbering of the various positions of the isothiazole ring is also indicated):

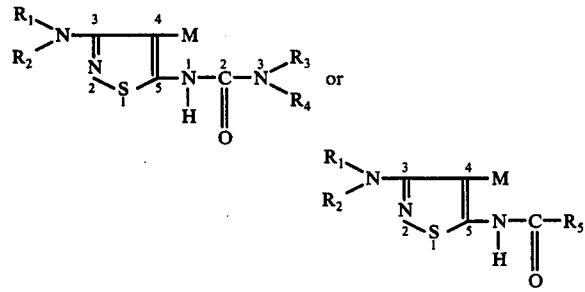

wherein
R$_1$ and R$_2$ are alkyl, alkenyl, cycloalkyl, aralkyl, or taken together form a divalent radical which may also contain a hetero atom,
R$_3$ is alkyl, cycloalkyl or methoxy,
R$_4$ is alkyl or hydrogen, or R$_3$ and R$_4$ taken together form a divalent radical which may also contain a hetero atom,
R$_5$ is alkyl, alkenyl, haloalkyl or haloalkenyl,
M is -CN,

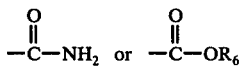

wherein R$_6$ is lower alkyl.

The alkyl, cycloalkyl, and alkenyl groups preferably have less than 10 carbon atoms; for R$_2$, R$_3$ and R$_4$ they preferably have less than 5 carbons, while for R$_5$ they preferably have less then 7 carbon atoms. Examples of alkyl groups are methyl, ethyl, propyl, isopropyl, isobutyl, sec-butyl, tert-butyl, 2-pentyl, and so on. The divalent radicals formed by R$_1$ and R$_2$, or R$_3$ and R$_4$, preferably contain a total of 4 or 5 catenated atoms, no more than one of which is oxygen, sulfur or nitrogen. In the most preferred compounds, both R$_3$ and R$_5$ are alkyl of 1 to 4 carbon atoms, R$_4$ is H and M is carboxamide.

Preparation of the compounds of the invention is described in the following examples. In the descriptions which follow, all temperatures are in degrees centigrade. All reduced pressures not otherwise designated are the pressures normally attainable using a water aspirator.

EXAMPLE I

1-Methyl-3-(4-cyano-3-(dimethylamino)-5-isothiazolyl)-urea

A. Di(sodiomercapto)methylenemalononitrile

A solution of 240 g of sodium hydroxide in 2700 ml of ethanol was cooled to approximately 10°, and 198.2 g of malononitrile were added dropwise during 30 minutes, keeping the reaction temperature between 5°–12°. Stirring was continued for 30 minutes at 12° after complete addition of malononitrile.

While a reaction temperature of 10°–15° was maintained, 228.4 g of carbon disulfide were added dropwise during 45 minutes. An additional 200 ml of ethanol were added to aid stirring. Upon complete addition of the carbon disulfide, the reaction was stirred for two hours while it warmed to ambient temperature. The thick yellow slurry was used without isolation.

B. 2-Cyano-3,3-bis(methylthio)propenenitrile

To the thick slurry of di(sodiomercapto)methylenemalononitrile were added dropwise 851.6 g of iodomethane. During addition, the exothermic reaction increased the temperature to 35°. The addition of iodomethane was stopped and the reaction was heated to 50°. The 50° reaction temperature was maintained by the continued addition of iodomethane, which required a total of two hours to complete. During this time, the yellow slurry became homogeneous and formed a dark-brown solution. After complete addition of iodomethane, the 50° reaction temperature was maintained for an additional 15 minutes. The reaction mixture was then stirred for 17 hours at ambient temperature.

The volume of the mixture was reduced by distillation at atmospheric pressure until 2300 ml of distillate had been collected. The residual mass was cooled and 3000 ml of ice-water were added to dissolve the sodium iodide by-product. The resulting slurry was stirred for 30 minutes, then filtered cold. The filter cake was washed with cold water to give 465 g of 2-cyano-3,3-bis(methylthio)propenenitrile, m.p. 75°–77°. The product was purified by recrystallizing from 1500 ml of methanol, after decolorizing with charcoal, to give 278.3 g of yellow-white solid, m.p. 79°–81°.

C. 3-Amino-2-cyano-3-(methylthio)propenenitrile

Two liters of ethanol were saturated with ammonia gas at 15°. At ambient temperature, 278.3 g of 2-cyano-3,3-bis(methylthio)propenenitrile were added portionwise. A sodium hydroxide trap was used to trap the methyl mercaptan by-product. After complete addition of the propenenitrile the reaction mixture was cooled to approximately 10°. The solid which separated was collected by filtration and washed with cold ethanol to give, after drying, 206.3 g of white 3-amino-2-cyano-3-(methylthio)propenenitrile, m.p. 228°–230°. The nmr was consistent with the assigned structure.

D. 3-Amino-2-cyano-3-(dimethylamino)propenenitrile

Into a pressure bottle were placed 5.6 g of 3-amino-2-cyano-3-(methylthio)propenenitrile and 3 ml of dimethylformamide, and the mixture was cooled to 0°. A volume of 5.4 ml (3.6 g) of dimethylamine was condensed in a dry-ice trap and added to the pressure bottle. The bottle was sealed and the reaction mixture was heated, with stirring, at 100° for 3–4 hours (in subsequent runs, the heating time was reduced to 80 minutes without reducing the yield). After this time, the mixture was allowed to cool to ambient temperature, where it stood for two days. The pressure bottle was cooled to 0° and opened. The mixture was allowed to attain ambient temperature, then was poured into 300 ml of ice-water, causing a white solid to precipitate. The slurry was stirred for 30 minutes. The solid product was collected by filtration and washed with cold water to give 5.1 g of 3-amino-2-cyano-3-(dimethylamino)propenenitrile, m.p. 228°–229°. The nmr was consistent with the assigned structure.

Analysis: Calc'd for $C_6H_8N_4$: C, 52.93; H, 5.92; N, 41.15; Found: C, 53.20; H, 5.87; N, 41.19.

E. 3-Amino-2-cyano-3-(dimethylamino)propenethioamide

To a solution of 5.4 g of 3-amino-2-cyano-3-(dimethylamino)propenenitrile and 4.0 g of triethylamine in 25 ml of dimethylformamide at 50° were added 11.6 g of aqueous hydrogen sulfide. Upon complete addition of hydrogen sulfide, the reaction mixture was heated at 65° for 1 hour. Since comparison by thin-layer chromatography of the reaction mixture with the starting material indicated that no reaction had taken place, the reaction temperature was increased to 80°, where it was maintained for two hours, but again no reaction occurred. A small amount of triethylamine and 1 g of hydrogen sulfide were added to the solution. Heating was then continued at 85°. After 30 minutes reaction (as determined by thin-layer chromatography) was 40% complete. Small increments of triethylamine and hydrogen sulfide were added as heating continued until, after 2½ hours at 85°, reaction was 95% complete. The solution was poured onto 150 ml of ice-water, and was purged with nitrogen gas to remove excess hydrogen sulfide. After 30 minutes, a solid formed, and was collected by filtration. The solid filter cake was washed with cold water and air-dried overnight to give 4.6 g of white solid 3-amino-2-cyano-3-(dimethylamino)propenethioamide, m.p. 186°–187°. The nmr spectrum was consistent with the assigned structure.

Analysis: Calc'd for $C_6H_{10}N_4S$: C, 42.35; H, 5.92; N, 32.92; Found: C, 42.50; H, 6.01; N, 33.11.

F. 5-Amino-4-cyano-3-(dimethylamino)isothiazole

A slurry of 5.1 g of 3-amino-2-cyano-3-(dimethylamino)propenethioamide and 25 ml of ethanol was heated to reflux (about 80°) while 3.8 ml of 30% hydrogen peroxide (1.1 g of active $H_2O_2$) were added dropwise; the exothermic reaction maintained the mixture at the reflux temperature. After addition of the peroxide was completed, the reaction mixture was heated under reflux for 30 minutes, then filtered hot and allowed to cool. The mixture was diluted with 100 ml of water and stirred for 15 minutes. The resulting precipitate, 5-amino-4-cyano-3-(dimethylamino)isothiazole, was collected by filtration.

A larger run was carried out in the same manner using 61.4 g of thioamide. The products were combined (62 g) and purified by column chromatography. The products were divided in half and each half was combined with 30 g of silica gel. Each sample was ground in a mortar and pestle. Two chromatography columns, each containing 250 g of silica gel (70–230 mesh, 4.4 × 58.4 cm), were prepared. Each sample was placed on a column and eluted with a 1:1 mixture of ethyl acetate and cyclohexane. The combined yield of 5-amino-4-cyano-3-(dimethylamino)isothiazole from the two columns was 48.9 g, m.p. 153°–154°. The nmr spectrum was consistent with the assigned structure.

Analysis: Calc'd for $C_6H_8N_4S$: C, 42.86; H, 4.80; N, 33.32; S, 19.03; Found: C, 43.18; H, 4.80; N, 32.67; S, 19.49.

G. 1-Methyl-3-(4-cyano-3-(dimethylamino)-5-isothiazolyl)-urea

Ten drops of dibutyltin diacetate were added to a solution of 3.0 g of 5-amino-4-cyano-3-(dimethylamino)isothiazole and 1.9 g of methyl isocyanate in 25 ml of tetrahydrofuran. The solution was heated under reflux for two hours, at which time thin-layer chromatographic analysis indicated the reaction to be 40% complete. After the addition of 5 ml more of dibutyltin diacetate and 2 ml more of methyl isocyanate, heating was continued for 90 minutes. Thin-layer chromatographic analysis indicated the reaction to be 60% complete. An additional 15 ml of tetrahydrofuran to dissolve the precipitate which had formed, 10 drops of dibutyltin diacetate, and 3 ml of methyl isocyanate were added and heating was continued for three hours. Thin-layer chromatographic analysis indicated approximately 90% conversion to the desired product. The reaction mixture was stirred at ambient temperature overnight, 2 ml more of methyl isocyanate were added, and the solution was heated under reflux for 1 hour. Thin-layer chromatographic analysis indicated 95% completion. The reaction mixture was cooled to −10°, the solid was collected by filtration and washed with water. Purification was accomplished by recrystallization from 300 ml of methanol to give a solid, m.p. 240°–241°. A second crop of solid, m.p. 240°–241°, was also collected to give a total yield of 6.2 g of 1-methyl-3-(4-cyano-3-(dimethylamino)-5-isothiazolyl)urea. The nmr spectrum was consistent with the assigned structure.

Analysis: Calc'd for $C_8H_{11}N_5SO$: C, 42.67; H, 4.92; N, 31.10; S, 14.24; Found: C, 42.78; H, 5.00; N, 30.86; S, 14.39.

EXAMPLE II 1,1-Dimethyl-3-(4-cyano-3-(dimethylamino)-5-isothiazolyl)urea

A. Phenyl (4-cyano-3-(dimethylamino)-5-isothiazolyl-carbamate

A mixture of 3.4 g of 5-amino-4-cyano-3-(dimethylamino)isothiazole and 4.7 g of phenyl chloroformate in 22 ml of toluene was heated at 100° for 45 minutes while being purged with nitrogen gas to remove by-product hydrogen chloride. Thin-layer chromatographic analysis of the reaction mixture indicated three constituents, one being the starting aminoisothiazole. An additional 4.7 g of phenyl chloroformate and 10 ml of toluene were added to the reaction mixture and the heating was continued for 16 hours.

Thin-layer chromatographic analysis of the reaction mixture again indicated three constituents. Two grams of triethylamine were added to the reaction mixture and the heating continued for 4½ hours. Thin-layer chromatographic analysis again indicated three constituents in the reaction mixture; however, the spot indicating the starting aminoisothiazole was less intense than previously. Fifteen drops of phenyl chloroformate and 10 drops of triethylamine were added and heating continued for an additional four and a half hours. The reaction mixture was allowed to cool to ambient temperature overnight, during which time a solid precipitate appeared. The reaction mixture was cooled to 5°, and the solid was collected by filtration and was washed with water. Recrystallization from ethanol and water gave 2.2 g of solid phenyl (4-cyano-3-(dimethylamino)-5-isothiazolyl)carbamate; m.p. 192°–193°. The nmr spectrum was consistent with the assigned structure.

Analysis: Calc'd for $C_{13}H_{12}N_4SO_2$: C, 54.17; H, 4.20; N, 19.44; S, 11.12; Found: C, 54.09; H, 4.41; N, 19.37; S, 11.00.

A large run was prepared in the same manner using 19.7 g of the aminoisothiazole to give 6.1 g of the desired product.

B.
1,1-Dimethyl-3-(4-cyano-3-(dimethylamino)-5-isothiazolyl)urea

In a pressure bottle were placed 6.1 g of phenyl (4-cyano-3-(dimethylamino)-5-isothiazolyl)carbamate and 25 ml of dimethylformamide. This solution was cooled to 0°, and 2.8 ml (1.9 g) of dimethylamine (previously collected in a graduated dropping funnel using a dry-ice trap) were added. The reaction mixture was heated at 80° for 4 hours, cooled to −10° and the bottle was opened. The reaction mixture was concentrated to dryness under vacuum to give a tan solid. Recrystallization of the tan solid from ethanol gave 4.0 g of 1,1-dimethyl-3-(4-cyano-3-(dimethylamino)-5-isothiazolyl)urea, m.p. 203°–204°. A second crop was collected and was recrystallized from ethanol to give 0.2 g of needles; m.p. 201°–202°. The nmr spectrum was consistent with the assigned structure.

Analysis: Calc'd for $C_9H_{13}N_5OS$: C, 45.19; H, 5.48; N, 29.27; S, 13.40; Found: C, 45.29; H, 5.48; N, 29.06; S, 13.37.

EXAMPLE III

1-Methyl-3-(4-carbamoyl-3-(dimethylamino)-5-isothiazolyl)urea.

A mixture of 11.2 g of 1-methyl-3-(4-cyano-3-(dimethylamino)-5-isothiazolyl)urea and 20 ml of concentrated sulfuric acid was heated at 85°–90° for 1½ hours. The reaction mixture was poured into 300 ml of ice-water and the solid precipitate was collected by filtration. The solid was washed with water and a small amount of cold ethanol. The nmr spectrum of this solid (m.p. 243°, decomposes) indicated it to be the bisulfate salt of 1-methyl-3-(4-carbamoyl-3-(dimethylamino)-5-isothiazolyl)urea. The water-sulfuric acid filtrate was concentrated under reduced pressure, the concentrate was cooled and a solid precipitate was collected by filtration. This solid was combined with the bisulfate salt described above and was stirred with a saturated solution of sodium bicarbonate. A new solid was collected by filtration and purified by recrystallization from ethanol to give 9.2 g of 1-methyl-3-(4-carbamoyl-3-(dimethylamino)-5-isothiazolyl)urea; m.p. 221°. The nmr spectrum was consistent with the assigned structure.

Analysis: Calc'd for $C_8H_{13}N_5SO_3$: C, 39.51; H, 5.39; N, 28.79; S, 13.18; Found: C, 39.67; H, 5.65; N, 28.51; S, 13.41.

EXAMPLE IV

1-Methyl-3-(4-cyano-3-(diethylamino)-5-isothiazolyl)urea

A. N-(Dichloromethylene)-N,N-diethylammonium chloride

At 20°–25°, a solution of 175 g of bis(diethylthiocarbamoyl) disulfide in 1350 ml of carbon tetrachloride was saturated with chlorine gas (521 g). The reaction mixture was cooled to 10° and purged with nitrogen gas. The precipitate was collected by filtration. The filter cake was washed with carbon tetrachloride until the washings were colorless. The hygroscopic product N-(dichloromethylene)-N,N-diethylammonium chloride was dried under reduced pressure over a weekend. Drying of the yellow solid continued at 50° on a rotary evaporator for 4 hours to give 209 g of product which was used without further purification.

B. 3-Chloro-2-cyano-3-(diethylamino)propenenitrile

A solution of 12.1 g of triethylamine, 4.0 g of malononitrile, and 20 ml of chlorobenzene was added to a slurry of 11.4 g of N-(dichloromethylene)-N,N-diethylammonium chloride and 50 ml of chlorobenzene, at ambient temperature. The reaction temperature was kept below 50° by controlling the rate of addition (time required for complete addition, 30 minutes). After addition, the reaction mixture was stirred for four hours while it returned to ambient temperature. The reaction mixture was filtered and the filtrate concentrated on the rotary evaporator to give a brownish-red liquid. Vacuum distillation gave 3.7 g of liquid 3-chloro-2-cyano-3-(diethylamino)propenenitrile; b.p. 127°–131°/0.05 mm Hg. The ir and nmr spectra were consistent with the assigned structure.

C. 3-Amino-2-cyano-3-(diethylamino)propenenitrile

A solution of 91.8 g of 3-chloro-2-cyano-3-(diethylamino)propenenitrile in 80 ml of ethanol was added to 400 ml of concentrated ammonium hydroxide at 25° during 45 minutes. After the addition, the reaction mixture was heated at 30°–35° for 2½ hours and allowed to stand overnight while it returned to ambient temperature. Thin-layer chromatographic analysis indicated a mixture of starting material and product. The reaction mixture was heated to 70° and gaseous ammonia was bubbled in during 3 hours. The reaction mixture was cooled in an ice-water bath and 200 ml of ice-water were added. The solid precipitate was collected by filtration and washed with water, then pentane. Recrystallization from ethanol gave a first crop of 72.8 g of pink needles, m.p. 170°–171°. A second crop of 3.3 g (m.p. 169°–171°) was collected from the ethanol mother liquor to give a total yield of 76.1 g of 3-amino-2-cyano-3-(diethylamino)propenenitrile. The nmr spectrum was consistent with the assigned structure.

Analysis: Calc'd for $C_8H_{12}N_4$: C, 58.52; H, 7.37; N, 34.12; Found: C, 58.37; H, 7.33; N, 34.19.

D.
3-Amino-2-cyano-3-(diethylamino)propenethioamide

A mixture of 72.6 g of 3-amino-2-cyano-3-(diethylamino)propenenitrile, 44.7 g of triethylamine, 200 ml of pyridine, and 50 ml of dimethylformamide was saturated at 60° with hydrogen sulfide. The temperature was increased to 75° while hydrogen sulfide was passed through the solution. After heating at 75° for 2 hours, thin-layer chromatographic analysis indicated the reaction was incomplete. After about 60 hours at room temperature the mixture was heated at 75° for an additional 4 hours. The mixture was allowed to cool to ambient temperature, then was poured into 1750 ml of ice-water mixture. The cold slurry was stirred for 1 hour and the solid was isolated by filtration. The solid was washed with ice-water and recrystallized from 250 ml of ethanol to give 56 g of 3-amino-2-cyano-3-(diethylamino)propenethioamide, m.p. 151°–152°. The nmr spectrum was consistent with the assigned structure.

Analysis: Calc'd for $C_8H_{14}N_4S$: C, 48.47; H, 7.13; N, 28.26; S, 16.14; Found: C, 48.59; H, 7.20; N, 27.99; S, 16.13.

E. 5-Amino-4-cyano-3-(diethylamino)isothiazole

Using the procedure of Example I, part F, 54.5 g of 3-amino-2-cyano-3-(diethylamino)propenethioamide were oxidized with 41 ml of 30% hydrogen peroxide to give 41.5 g of white 5-amino-4-cyano-3-(diethylamino)isothiazole, m.p. 87°–88°. The nmr spectrum was consistent with the assigned structure.

Analysis: Calc'd for $C_8H_{12}N_4S$: C, 48.97; H, 6.16; N, 28.55; S, 16.31; Found: C, 49.06; H, 6.27; N, 28.32; S, 16.46.

F.
1-Methyl-3-(4-cyano-3-(diethylamino)-5-isothiazolyl)urea

A mixture of 9.8 g of 5-amino-4-cyano-3-(diethylamino)isothiazole, 20 drops of dibutyltin diacetate, and about 15 ml of methyl isocyanate in 50 ml of dry tetrahydrofuran was heated under reflux for 21 hours, at which time thin-layer chromatographic analysis indicated reaction to be complete. The solution was concentrated under reduced pressure and the residue was recrystallized from ethanol to give 11.7 g of white 1-methyl-3-(4-cyano-3-(diethylamino)-5-isothiazolyl)urea, m.p. 182°–183°. The nmr spectrum was consistent with the assigned structure.

Analysis: Calc'd for $C_{10}H_{15}N_5OS$: C, 47.43; H, 5.97; N, 27.65; S, 12.64; Found: C, 47.45; H, 6.03; N, 27.75; S, 12.93.

EXAMPLE V
1-Methyl-3-(4-carbamoyl-3-(diethylamino)-5-isothiazolyl)urea

A stirred mixture of 8.5 g of 1-methyl-3-(4-cyano-3-(diethylamino)-5-isothiazolyl)urea in 17 ml of concentrated sulfuric acid was heated at 100° during 1¼ hours. The reaction mixture was poured into 250 ml of stirred ice-water. The mixture became unstirrable and was then carefully poured into 1 liter of saturated sodium bicarbonate solution. The mixture was stirred during one and a quarter hours, filtered cold, and washed with cold water. The collected solid was recrystallized twice from ethanol to give 5.3 g of 1-methyl-3-(4-carbamoyl-3-(diethylamino)-5-isothiazolyl)urea; m.p. 195°–197°. The nmr spectrum was consistent with the assigned structure.

Analysis: Calc'd for $C_{10}H_{17}N_5O_2S$: C, 44.28; H, 6.32; N, 25.82; S, 11.80; Found: C, 44.20; H, 6.26; N, 25.97; S, 11.90.

EXAMPLE VI
1-Methyl-3-(4-cyano-3-(1-pyrrolidinyl)-5-isothiazolyl)urea

A. Dibromomalononitrile-potassium bromide complex

A mixture of 99 g of malononitrile and 75 g of potassium bromide in 900 ml of water was cooled to 5°–10° and 158 ml of bromine were slowly added at 5°–10° during 2½ hours. After addition was completed, the mixture was stirred for 2 hours at 5°–10°, then was filtered. The collected solid was washed with 150 ml of ice-water and air-dried on the filter. A second crop was obtained by filtering the filtrate after a short quiescent period. The isolated solids were combined and dried to constant weight in a desiccator over phosphorus pentoxide (the presence of bromine vapors necessitated replenishing the phosphorus pentoxide) to give 337.5 g of the complex, which was used without further purification.

B. Potassium tricyanomethanide

A mixture of 173.4 g of potassium cyanide and 1400 ml of 1,2-dimethoxyethane was stirred for 15 minutes at ambient temperature, then cooled to 10°–20°. Into the cold mixture was added 337.5 g of the dibromomalononitrile-potassium bromide complex from part A (above) in small portions during 1 hour. The mixture was stirred at room temperature for two hours, then brought to reflux temperature. The hot solution was filtered through a steam-jacketed funnel and the filtrate cooled to ambient temperature. Two liters of diethyl ether were added and the mixture cooled to about 10°. The slurry was filtered, the solid was washed with ether and dried overnight to give 135.5 g of potassium tricyanomethanide.

C. 3-Amino-2-cyano-3-(1-pyrrolidinyl)propenenitrile

A suspension of 122 g of potassium tricyanomethanide, 325 ml of water and 1135 ml of diethyl ether was stirred and cooled to 5°–10°. To the cold mixture was added dropwise with efficient stirring at 5°–10° 95 g of concentrated sulfuric acid. The mixture was stirred for one hour and 150 ml of diethyl ether was added. The three layers were separated and the ether layer (usually middle layer) used without further treatment.

To the ether layer were added dropwise during 15 minutes at room temperature 67.6 g of pyrrolidine. The mixture was stirred for ½ hour at 20°–25°, then was concentrated under reduced pressure. The residue was heated on a steam bath overnight under reduced pressure. On cooling, the solidified residue was stirred with 500 ml of cold water and the solid was isolated by filtration to give 42.9 g of solid, m.p. 174°–175°.

The filtrate was concentrated and the residue was heated at about 150° for 2 hours. The reaction mixture was then cooled and 200 ml of ice-water were added.

The slurry was filtered to give 53.6 g of solid, m.p. 173°–174°.

The filtrate was again concentrated and the residue was heated again at about 150° for 2½ hours. The residue was cooled, ice-water was added with stirring and, after filtration and drying to constant weight, 30.0 g of solid were obtained, m.p. 158°–162°. The total yield of 3-amino-2-cyano-3-(1-pyrrolidinyl)propenenitrile was 126.5 g, which was used without further treatment.

D.
3-Amino-2-cyano-3-(1-pyrrolidinyl)propenethioamide

A mixture of 93.3 g of 3-amino-2-cyano-3-(1-pyrrolidinyl)propenenitrile, 58.2 g of triethylamine and 400 ml of pyridine was heated at 60°–65° and hydrogen sulfide passed in for 2½ hours. While continuing the addition of hydrogen sulfide, the temperature of the mixture was increased to 80°, where it was maintained for two and a half hours. The mixture stood for 64 hours at ambient temperature, then was heated at 90° for 2½ hours. The mixture was concentrated under reduced pressure. The tan solid residue was stirred with 750 ml of ice-water, the cold slurry was filtered and the solid was washed with cold water. The washed solid was recrystallized from 1200 ml of ethanol to give 87.4 g (three crops) of 3-amino-2-cyano-3-(1-pyrrolidinyl)propenethioamide, m.p. 164°. The nmr spectrum was consistent with the assigned structure.

Analysis: Calc'd for $C_8H_{12}N_4S$: C, 48.97; H, 6.16; N, 28.55; Found: C, 49.20; H, 6.27; N, 28.70.

E. 5-Amino-4-cyano-3-(1-pyrrolidinyl)isothiazole

Using the procedure of Example I, part F, 81.7 g of 3-amino-2-cyano-3-(1-pyrrolidinyl)propenethioamide were oxidized with 48 ml of 30% hydrogen peroxide to give 71.2 g of 5-amino-4-cyano-3-(1-pyrrolidinyl)isothiazole, m.p. 198°. The nmr spectrum was consistent with the assigned structure.

Analysis: Calc'd for $C_8H_{10}N_4S$: C, 49.48; H, 5.19; N, 28.85; Found: C, 49.78; H, 5.30; N, 29.02.

F.
1-Methyl-3-(4-cyano-3-(1-pyrrolidinyl)-5-isothiazolyl)urea

A mixture of 16.0 g of 5-amino-4-cyano-3-(1-pyrrolidinyl)isothiazole, 25 drops of dibutyltin diacetate and 5.4 g of methyl isocyanate in 90 ml of tetrahydrofuran was heated under reflux for about 56 hours. Small increments of methyl isocyanate (3 ml at 27 hours and 2 ml at 40 hours) and dibutyltin diacetate (10 drops at 32 hours and 5 drops at 40 hours) were added during the reflux period. A solid that had formed was isolated by filtration. The filtrate was concentrated under reduced pressure to obtain a second crop. A total of 17.0 g of 1-methyl-3-(4-cyano-3-(1-pyrrolidinyl)-5-isothiazolyl)urea, m.p. 239°, was obtained. The nmr spectrum was consistent with the assigned structure.

Analysis: Calc'd for $C_{10}H_{13}N_5SO$: C, 47.81; H, 5.22; N, 27.87; Found: C, 47.95; H, 5.50; N, 28.14.

EXAMPLE VII
1-Methyl-3-(4-carbamoyl-3-(1-pyrrolidinyl)-5-isothiazolyl)urea A stirred mixture of 10.5 g of 1-methyl-3-(4-cyano-3-(1-pyrrolidinyl)-5-isothiazolyl)urea and 15 ml of sulfuric acid was heated at 100° during 2½ hours. The mixture was poured into 250 ml of stirred ice-water and neutralized by slow addition of saturated sodium bicarbonate solution. The separated solid was collected by filtration. The filtrate was allowed to stand for a short time, and filtered again. The collected solid was found to be a mixture of the desired product and unreacted starting material. A third solid that formed when the filtrate was allowed to stand overnight was isolated by filtration to give 4.6 g of 1-methyl-3-(4-carbamoyl-3-(1-pyrrolidinyl)-5-isothiazolyl)urea, which darkened at 241°, then decomposed at 257°. The nmr spectrum was consistent with the assigned structure.

Analysis: Calc'd for $C_{10}H_{15}N_5O_2S$: C, 44.61; H, 5.62; N, 26.01; Found: C, 44.38; H, 5.90; N, 26.28.

EXAMPLE VIII
1-Methyl-3-(4-cyano-3-(dipropylamino)-5-isothiazolyl)urea

A. 3-Amino-2-cyano-3-(dipropylamino)propenenitrile

In the manner of Example VI, part C, 25 g of potassium tricyanomethanide in 75 ml of water and 100 ml of diethyl ether were treated with 19 g of concentrated sulfuric acid to give an ether solution of $HN=C=C(CN)_2$. The ether solution was treated with 19.6 g of dipropylamine and the mixture allowed to stand for ½ hour. The ether was removed by distillation under reduced pressure and the residue heated to 150°. To the hot residue were added 500 ml of aqueous ethanol and the mixture was boiled vigorously for 15 minutes. The mixture was again concentrated and the residue heated at 150° for about 16 hours. The mixture was dissolved in aqueous ethanol, treated with activated charcoal and chilled for two days at about 5°. The separated solid was collected by filtration and dried to give 31 g of 3-amino-2-cyano-3-(dipropylamino)propenenitrile, m.p. 100°–105° from toluene. The ir and nmr spectra were consistent with the assigned structure.

Analysis: Calc'd for $C_{10}H_{16}N_4$: C, 62.47; H, 8.39; N, 29.14; Found: C, 62.33; H, 8.54; N, 29.40.

B.
3-Amino-2-cyano-3-(dipropylamino)propenethioamide

An attempt at conversion by the method of Example IV, part D, was unsuccessful. Thus a mixture of 28 g of 3-amino-2-cyano-3-(dipropylamino)propenenitrile, 14.7 g of triethylamine and 100 ml of pyridine in a pressure bottle was cooled to −70° and 10 g of hydrogen sulfide were added. The bottle was capped and allowed to stand at ambient temperature during two days, then heated at 80° for about 16 hours. The mixture was concentrated under reduced pressure and the residue was dissolved in a minimum of toluene containing a trace of ethanol. The solid which separated on cooling was collected to obtain 9.6 g of 3-amino-2-cyano-3-(dipropylamino)propenethioamide, m.p. 141°–144°. The nmr spectrum was consistent with the assigned structure.

C. 5-Amino-4-cyano-3-(dipropylamino)isothiazole

A solution of 9.6 g of 3-amino-2-cyano-3-(dipropylamino)propenethioamide in 50 ml of ethanol was heated to reflux temperature and 5 ml of 30% hydrogen peroxide (1.4 g $H_2O_2$) were added at such a rate as to maintain reflux. After complete addition the reaction mixture was heated under reflux during 10 minutes. To the reaction mixture was added 40 ml of water, which was then allowed to cool to ambient temperature. The solid precipitate was collected by filtration, and recrystallized from acetonitrile-water, to give 7.0 g of 5-amino-4-cyano-3-(dipropylamino)isothiazole; m.p. 136°–138°. The nmr and ir spectra were consistent with the assigned structure.

Analysis: Calc'd for $C_{10}H_{16}N_4S$: C, 53.54; H, 7.19; N, 24.98; S, 14.29; Found: C, 53.76; H, 7.30; N, 24.68; S, 14.25.

D.
1-Methyl-3-(4-cyano-3-(dipropylamino)-5-isothiazolyl)urea

A solution of 7.0 g of 5-amino-4-cyano-3-(dipropylamino)isothiazole, 3.6 g of methyl isocyanate and 40 drops of dibutyltin diacetate in 50 ml of tetrahydrofuran was heated under reflux overnight. Thin-layer chromatographic analysis indicated the reaction to be complete. The reaction mixture was poured into rapidly stirred, cold water. The solid precipitate was collected by filtration. The filtrate was extracted with methylene chloride. The solid was combined with the extract and the mixture dried over calcium chloride, then filtered through magnesium sulfate. The filtrate was concentrated under reduced pressure and the residue was taken up in a mixture of toluene and benzene to which a little ethanol had been added. Pentane was then added to promote crystallization. The recrystallization yielded 6.2 g of 1-methyl-3-(4-cyano-3-(dipropylamino)-5-isothiazolyl)urea, m.p. 179°–180°. The nmr and ir spectra were consistent with the assigned structure.

Analysis: Calc'd for $C_{12}H_{19}N_5OS$: C, 51.22; H, 6.81; N, 24.89; S, 11.39; Found: C, 51.47; H, 7.10; N, 25.07; S, 11.20.

EXAMPLE IX
1-Methyl-3-(4-carbamoyl-3-(dipropylamino)-5-isothiazolyl)urea 1-Methyl-3-(4-cyano-3-(dipropylamino)-5-isothiazolyl)urea (4.2 g) was slowly stirred into 10 ml of concentrated sulfuric acid and the resulting solution was warmed to 80° where it was maintained for about 16 hours. The solution was poured into 200 ml of ice-water and the solution was brought to pH 10 by adding a mixture of sodium bicarbonate, sodium carbonate, and ammonium hydroxide. The white precipitate was collected by filtration, but thin-layer chromatographic analysis showed the white solid to be a mixture of starting material and product. The solid was again placed in 10 ml of concentrated sulfuric acid. The solution was heated on a steam bath and then poured into 100 ml of water. This mixture was brought to pH 10 with aqueous ammonium hydroxide. The solid precipitate was collected by filtration and dried to give 4.2 g of 1-methyl-3-(4-carbamoyl-3-(dipropylamino)-5-isothiazolyl)urea, m.p. 168°–169°. The nmr and ir spectra were consistent with the assigned structure.

Analysis: Calc'd for $C_{12}H_{21}N_5O_2S$: C, 48.14; H, 7.07; N, 23.39; S, 10.71; Found: C, 48.37; H, 6.90; N, 23.01; S, 10.50.

EXAMPLE X
N-(4-Cyano-3-(diethylamino)-5-isothiazolyl)propanamide

A solution of 9.8 g of 5-amino-4-cyano-3-(diethylamino)isothiazole and 13.1 g of propionic anhydride was heated under reflux for three hours, then stirred for two days at ambient temperature. The reaction mixture was poured into 300 ml of saturated sodium bicarbonate and stirred for 30 minutes. The solid precipitate was collected by filtration, washed with water and recrystallized from ethanol to give 11.5 g of crystalline N-(4-cyano-3-(diethylamino)-5-isothiazolyl)propanamide; m.p. 188°–189°. The nmr spectrum was consistent with the assigned structure.

Analysis: Calc'd for $C_{11}H_{16}N_4OS$: C, 52.37; H, 6.39; N, 22.21; S, 12.70; Found: C, 53.27; H, 6.37; N, 22.09; S, 12.47.

EXAMPLE XI
1-Methyl-3-(4-cyano-3-(ethylmethylamino)-5-isothiazolyl)urea

A.
3-Amino-2-cyano-3-(ethylmethylamino)propenenitrile

An attempted preparation by the method of Example VI, part C, was unsuccessful. Thus, a mixture of 129 g of potassium tricyanomethanide, 59 g of ethylmethylamine, and 2000 ml of dimethoxyethane was treated with 65 ml (96 g) of methanesulfonic acid added dropwise during 30 min. The reaction was mildly exothermic and solid formation was noted during addition of the methanesulfonic acid. The reaction mixture was heated under reflux for one hour and was allowed to stand two days at ambient temperature. The solids were removed by filtration and the filter cake was washed with toluene. The combined filtrate and washings were evaporated under reduced pressure. The residue was heated to 200° in an oven. The residue was removed from the oven and water was added immediately. The near boiling aqueous suspension was treated with charcoal and filtered through a mat of Filter-Aid ® diatomaceous earth in a large, steam heated, Buchner funnel. The aqueous filtrate was allowed to cool, producing crystals. The crystals were collected by filtration, dried, and recrystallized from acetonitrile to yield 86 g of 3-amino-2-cyano-3-(ethylmethylamino)propenenitrile, mp 140°–141°. The ir spectrum was consistent with the assigned structure.

B.
3-Amino-2-cyano-3-(ethylmethylamino)propenethioamide

In a 50-ml, 3-necked, round-bottom flask equipped with a mechanical stirrer, a gas delivery tube, thermometer, condenser, and exit tube fitted with a rubber balloon were placed 7.5 g of 3-amino-2-cyano-3-(ethylmethylamino)propenenitrile, 14 ml (10.1 g) of triethylamine and 15 ml of pyridine. Hydrogen sulfide gas was bubbled into the solution until saturation was evidenced by inflation of the rubber balloon. The solution was heated at 50° C on a steam bath during gas addition. The reaction was monitored by infra-red spectrographic observation. Complete reaction was evidenced by the disappearance of the nitrile absorption band at 4.57µ. After the solution was mixed thoroughly at 50° C, the reaction was allowed to continue at room temperature under an atmosphere of hydrogen sulfide for approximately 48 hours. At this point the 4.57µ absorption band had disappeared from the infra-red spectrum. The reaction mixture was evaporated under reduced pressure and the residue was recrystallized from ethyl acetate to yield 4.6 g of 3-amino-2-cyano-3-(ethylmethylamino)-propenethioamide, mp 121°–124°. The ir and nmr spectra were consistent with the assigned structure.

Analysis: Calc'd for $C_7H_{12}N_4S$: C, 45.63; H, 6.57; N, 30.41; S, 17.40; Found: C, 45.72; H, 6.77; N, 30.49; S, 17.60.

A larger run was carried out in the same manner using 61.3 g of the nitrile to produce an additional 56 g of 3-amino-2-cyano-3-(ethylmethylamino)propenethioamide, mp 120°–123°.

C. 5-Amino-4-cyano-3-(ethylmethylamino)isothiazole

A mixture containing 60 g of 3-amino-2-cyano-3-(ethylmethylamino)propenethioamide and 250 ml of ethanol was heated to reflux, while 40 ml of 30% hydrogen peroxide (11.1 g of active $H_2O_2$) were added dropwise at such a rate as to maintain an even reflux. After the peroxide addition was completed, the reaction mixture was heated for 30 minutes. Charcoal was added to the hot solution. The charcoal was removed by filtration and the filtrate was evaporated under reduced pressure. The residue was recrystallized from toluene to yield 51 g of 5-amino-4-cyano-3-(ethylmethylamino)isothiazole, mp 94°–95°. The ir and nmr spectra were consistent with the assigned structure.

Analysis: Calc'd for $C_7H_{10}N_4S$: C, 46.13; H, 5.53; N, 30.74; S, 17.59; Found: C, 46.26; H, 5.76; N, 30.49; S, 17.77.

D.
1-Methyl-3-(4-cyano-3-ethylmethylamino-5-isothiazolyl)urea

A mixture of 11 g of 5-amino-4-cyano-3-(ethylmethylamino)isothiazole, 6.8 g of methyl isocyanate, 2 ml of dibutyltin diacetate, and 50 ml of tetrahydrofuran was heated under reflux overnight. After cooling, the solution was evaporated under reduced pressure. The residue was recrystallized from toluene to yield 9.8 g of 1-methyl-3-(4-cyano-3-(ethylmethylamino)-5-isothiazolyl)urea, mp 175°. The ir and nmr spectra were consistent with the assigned structure.

Analysis: Calc'd for $C_9H_{13}N_5OS$: C, 45.18; H, 5.47; N, 29.27; S, 13.40; Found: C, 45.32; H, 5.55; N, 29.28; S, 13.12.

EXAMPLE XII 1,1-Dimethyl-3-(4-cyano-3-(ethylmethylamino)-5-isothiazolyl)urea

A. Phenyl (4-cyano-3-(ethylmethylamino)-5-isothiazolyl)carbamate

A mixture of 125 ml of toluene and 19.7 g of pinene was dried by distilling until 25 ml of distillate was obtained. The mixture was cooled and 25 g of 5-amino-4-cyano-3-(ethylmethylamino)isothiazole were added, followed by the slow and careful addition of 22.6 g of phenyl chloroformate. The reaction mixture was heated under reflux overnight. Thin-layer chromatographic analysis indicated that the reaction was complete. The volatile materials were removed under reduced pressure. The residue was taken up in diethyl ether. An unidentified yellow solid precipitated from the ether solution and was removed by filtration. Pentane was added to the filtrate to the cloud point giving crystals of phenyl (4-cyano-3-(ethylmethylamino)-5-isothiazolylcarbamate which formed on standing. The nmr spectrum was consistent with the assigned structure.

B.
1,1-Dimethyl-3-(4-cyano-3-(ethylmethylamino)-5-isothiazolyl)urea

A solution of 10.6 g of phenyl (4-cyano-3-(ethylmethylamino)-5-isothiazolyl)carbamate and 25 ml of dimethylformamide was placed in a pressure bottle. This solution was cooled and 5 ml of dimethylamine (previously collected in a dry-ice trap) were added. The pressure bottle was sealed and allowed to warm slowly to room temperature. The reaction mixture was then heated at 80° for approximately 16 hours. The reaction mixture was cooled in a dry ice bath and the vessel was opened. The reaction mixture was concentrated under reduced pressure until a small amount of material crystallized. Collection of the crystals produced 2.3 g of 1,1-dimethyl-3-(4-cyano-3-(ethylmethylamino)-5-isothiazolyl)urea, mp 115°–130° (decomposes). The ir and nmr spectra were consistent with the assigned structure.

Analysis: Calc'd for $C_{10}H_{15}N_5OS$: C, 47.41; H, 5.97; N, 27.64; S, 12.66; O, 6.32; Found: C, 47.16; H, 5.97; N, 27.90; S, 12.72.

EXAMPLE XIII

1-Methyl-3-(4-carbamoyl-3-(ethylmethylamino)-5-isothiazolyl)urea

A mixture of 6.8 g of 1-methyl-3-(4-cyano-3-(ethylmethylamino)-5-isothiazolyl)urea and 20 ml of concentrated sulfuric acid was prepared by addition of small portions of the isothiazolylurea to the rapidly stirred sulfuric acid during a 15 minute period at ambient temperature. Stirring of the mixture was continued until a homogeneous solution was obtained. The solution was heated at 50° in a thermostated water bath for 1 hour. The reaction mixture was poured into 200 ml of icewater and the resulting slurry was made strongly basic (pH 14) by addition of concentrated ammonium hydroxide. The temperature was maintained at 0° by addition of the ice during the pH adjustment process. The solid was collected by filtration and the filter cake dried. The solid was recrystallized from ethyl acetate to yield 4.4 g of 1-methyl-3-(4-carbamoyl-3-(ethylmethylamino)-5-isothiazolyl)urea, mp 165°–168°. The ir and nmr spectra were consistent with the assigned structure.

Analysis: Calc'd for $C_9H_{15}N_5O_2S$: C, 42.01; H, 5.88; N, 27.22; S, 12.46; O, 12.44 Found: C, 42.41; H, 5.94; N, 27.05; S, 12.01.

EXAMPLE XIV

1-Methyl-3-(3-(butylmethylamino)-4-cyano-5-isothiazolyl)urea

A.
3-Amino-3-(butylmethylamino)-2-cyanopropenenitrile

Methanesulfonic acid (65 ml; 96 g) was added dropwise during 30 minutes to a solution of 87 g of butylmethylamine in 1000 ml of diethyl ether. The diethyl ether was separated from the resulting butyl(methyl)ammonium methanesulfonate in a separatory funnel. The butyl(methyl)ammonium methanesulfonate was mixed with 129 g of potassium tricyanomethanide in a stainless steel bowl. The mixture was heated at 150° in an oven for approximately 16 hours. The residue was mixed with 2500 ml of boiling water for 30 minutes and filtered. The filter cake was then washed three times with 750 ml portions of boiling isopropanol. The aqueous filtrate produced a small amount of solid material upon cooling. This material was collected and combined with the solid from the cooled isopropanol filtrate. The combined solids were recrystallized from isopropanol to yield 77 g of 3-amino-3-(butylmethylamino)-2-cyanopropenenitrile, mp 160°–161°.

Analysis: Calc'd for $C_9H_{14}N_4$: C, 60.65; H, 7.92; N, 31.43; Found: C, 60.35; H, 7.75; N, 31.70.

B.
3-Amino-3-(butylmethylamino)-2-cyanopropenethioamide

A mixture of 75 g of 3-amino-3-(butylmethylamino)-2-cyanopropenenitrile, 86 g of triethylamine, and 150 ml of pyridine was heated at 60°–80° on a steam bath. During a six hour period 15 g of hydrogen sulfide gas was bubbled through the heated solution. The steam bath was removed and the addition of hydrogen sulfide gas was continued at ambient temperature for one day. The reaction mixture was allowed to stand at ambient temperature for several days. The mixture was evaporated to dryness under reduced pressure. The residue was recrystallized from isopropanol to yield 63 g of 3-amino-3-(butylmethylamino)-2-cyanopropenethioamide, mp 163°–165°. The nmr spectrum is consistent with the assigned structure.

Analysis: Calc'd for $C_9H_{16}N_4S$: C, 50.91; H, 7.60; N, 26.39; S, 15.10; Found: C, 51.15; H, 7.64; N, 26.36; S, 15.17.

C. 5-Amino-3-(butylmethylamino)-4-cyanoisothiazole

In the manner of Example XI, part C, 61 g of 3-amino-3-(butylmethylamino)-2-cyanopropenethioamide in 200 ml of ethanol were treated with 33 ml of 30% hydrogen peroxide (9.8 g of active $H_2O_2$) to yield 45 g of 5-amino-3-(butylmethylamino)-4-cyanoisothiazole, mp 87°–89°. The ir and nmr spectra were consistent with the assigned structure.

Analysis: Calc'd for $C_9H_{14}N_4S$: C, 51.40; H, 6.71; N, 26.64; S, 15.24; Found: C, 50.91; H, 6.72; N, 26.65; S, 14.36; 2d Sample Found: C, 51.54; H, 6.87; N, 26.90; S, 14.92.

D.
1-Methyl-3-(3-butylmethylamino)-4-cyano-5-isothiazolyl)urea

In the manner of Example XI, part D, 7 g of 5-amino-3-(butylmethylamino)-4-cyanoisothiazole, 4.1 ml (4 g) of methyl isocyanate, and a catalytic amount of dibutyltin diacetate in 50 ml of tetrahydrofuran were allowed to react. The volatile materials were removed under reduced pressure and the residue was crystallized from 35 ml of 70:30 diethyl ether:hexane to yield solid material, mp 102° (decomposes). This material was recrystallized from 70 ml of 40:60 diethylether:hexane to yield 4.1 g of 1-methyl-3-(3-(butylmethylamino)-4-cyano-5-isothiazolyl)urea mp 169°–170°. The nmr spectrum was consistent with the assigned structure.

Analysis: Calc'd for $C_{11}H_{17}N_5OS$: C, 49.42; H, 6.41; N, 26.20; S, 11.99; O, 5.98; Found: C, 49.13; H, 6.41; N, 25.93; S, 11.89.

EXAMPLE XV
1-Methyl-3-(3-(butylmethylamino)-4-carbamoyl-4-isothiazoyl)urea A mixture of 2 g of 1-methyl-3-(3-(butylmethylamino)-4-cyano-5-isothiazolyl)urea and 4 ml of concentrated sulfuric acid was heated at 80° for 1 hour. The reaction mixture was poured into 200 ml of ice cold ammonium hydroxide. The solid material was collected and recrystallized from cyclohexane to yield 1.5 g of 1-methyl-3-(3-(butylmethylamino)-4-cyano-5-isothiazolyl)urea, mp 109°–110°. The ir and nmr spectra are consistent with the assigned structure.

Analysis: Calc'd for $C_{11}H_{19}N_5O_2S$: C, 46.30; H, 6.71; N, 24.54; S, 11.23; O, 11.21; Found: C, 46.59; H, 6.77; N, 23.20; S, 11.07.

EXAMPLE XVI
1-Methyl-3-(3-(benzylethylamino)-4-cyano-5-isothiazolyl)urea

A.
3-Amino-3-(benzylethylamino)-2-cyanopropenenitrile

To a stirred solution of 13.5 g of (benzyl)(ethyl)amine in 200 ml of diethyl ether were added 6.5 ml (9.6 g) of methanesulfonic acid. The (benzyl)(ethyl)methaneammonium sulfonate salt was collected by filtration and dried. The dried salt was mixed with 12.9 g of potassium tricyanomethanide and heated at 150° in an oven for approximately 16 hours. The solid mass was taken up in 200 ml of hot 75:25 ethanol:water and filtered while hot through charcoal. The filtrate was cooled, and the resulting solids were collected by filtration and dried. The solid material was recrystallized from 150 ml of absolute ethanol to yield 12.3 g of 3-amino-3-(benzylethylamino)-2-cyanopropenenitrile, mp 165°–167°.

Analysis: Calc'd for $C_{13}H_{14}N$: C, 69.00; H, 6.24; N, 24.76; Found: C, 68.73; H, 6.45; N, 24.47.

In a similar manner 27.4 g of benzylethylamine and 13 ml (19.2 g) of methanesulfonic acid were allowed to react. The resulting salt was treated with 25.8 g of potassium tricyanomethanide to yield an additional 32 g of 3-amino-3-(benzylethylamino)-2-cyanopropenenitrile, mp 165°–167°.

B.
3-Amino-3-(benzylethylamino)-2-cyanopropenethioamide

In a 250-ml, 3-necked flask, equipped with a mechanical stirrer, gas inlet, condenser and a thermometer, were placed 41.2 g of 3-amino-3-(benzylethylamino)-2-cyanopropenenitrile and 90 ml of pyridine. The mixture was stirred until a homogeneous solution was achieved. To the solution were added 51 ml (36.9 g) of triethylamine. The mixture was heated at 60° and a slow stream of hydrogen sulfide gas was bubbled through the heated solution for approximately 56 hours. The mixture was evaporated to dryness under reduced pressure. The residue was crystallized from ethanol to yield 34.2 g of 3-amino-3-(benzylethylamino)-2-cyanopropenethioamide, mp 149°–151°. The ir and nmr spectra were consistent with the assigned structure.

Analysis: Calc'd for $C_{13}H_{16}N_4S$: C, 59.97; H, 6.20; N, 21.52; S, 12.31; Found: C, 59.77; H, 6.15; N, 21.80; S, 12.27.

C. 5-Amino-3-(benzylethylamino)-4-cyanoisothiazole

In the manner of Example XI, part C, 31.2 g of 3-amino-3-(benzylethylamino)-2-cyanopropenenitrile in 100 ml of ethanol were treated with 15 ml of 30% hydrogen peroxide (4 g of active $H_2O_2$) to yield 25.0 g of 5-amino-3-(benzylethylamino)-4-cyanoisothiazole, mp 103°–105°. The ir and nmr spectra are consistent with the assigned structure.

Analysis: Calc'd for $C_{13}H_{14}N_4S$: C, 60.44; H, 5.46; N, 21.69; S, 12.41; Found: C, 60.33; H, 5.44; N, 21.54; S, 12.19.

D. 1-Methyl-3-(3-(benzylethylamino)-4-cyano-5-isothiazolyl)urea

In the manner of Example XI, part D, 22 g of 5-amino-3-(benzylethylamino)-4-cyanoisothiazole, 9.7 g of methyl isocyanate, 3 ml of dibutyltin diacetate dissolved in 150 ml of tetrahydrofuran were allowed to react. The mixture was evaporated under reduced pressure and the residue was recrystallized from ethyl acetate to yield 13.9 of 1-methyl-3-(3-(benzylethylamino)-4-cyano-4-isothiazolyl)urea, mp 195°–196°. The ir and nmr spectra were consistent with the assigned structure.

Analysis: Calc'd for $C_{15}H_{18}N_5OS$: C, 56.94; H, 5.73; N, 22.13; S, 10.13; O, 5.06; Found: C, 57.15; H, 5.51; N, 21.90; S, 9.85.

The herbicidal activities of the compounds of this invention were demonstrated as follows. In preemergence tests, rows of seeds of lima beans (*Phaselous lunatus*), corn (*Zea mays*), wild oats (*Avena fatua*), lettuce (*Lactuca sativa*), mustard (*Brassica juncea*) and crabgrass (*Digitaria sanguinalis*) were planted in shallow flat-bed trays (20 cm × 15 cm × 7.5 cm) containing 5 cm to 7.5 cm of sandy loam soil. Within 24 hours after planting, an aqueous acetone solution of the compound (using sufficient acetone to obtain solution) was sprayed on the soil at a rate equivalent to 8.96 kilograms per hectare, using a total volume equivalent to 760 liters per hectare. The trays were maintained under normal growing conditions in the greenhouse for about three weeks, after which the herbicidal efficacy of the compound was assessed. Individual plant species were examined in comparison with untreated plants. Table 1 lists data collected in preemergence tests with compounds of the present invention.

In postemergence tests, rows of seeds were planted as for preemergence tests and the untreated flats were maintained in the greenhouse until the first trifoliate leaves of the bean plants were unfolding. The test plants were then sprayed with an aqueous acetone solution of the compound as for preemergence tests. The plants were returned to the greenhouse and held under normal growing conditions for about three more weeks, after which the herbicidal efficacy of the compound was assessed. Table 2 lists data collected in postemergence tests with compounds of the present invention.

Table 1
Preemergence Herbicidal Activity of 3-(substituted amino) isothiazolylureas and -alkanamides (expressed as percent kill at 8.96 kg/hectare)

| Compound of Example | Lima Bean | Corn | Wild Oats | Lettuce | Mustard | Crabgrass |
|---|---|---|---|---|---|---|
| I | 100 | 0 | 70 | 100 | 100 | 90 |
| II | 100 | 0 | 100 | 100 | 100 | 100 |
| III | 100 | 100 | 100 | 100 | 100 | 100 |
| IV | 100 | 0 | 100 | 100 | 80 | 100 |
| V | 100 | 100 | 100 | 100 | 100 | 50 |
| VI | 75 | 0 | 30 | 70 | 30 | 0 |
| VII | 100 | 70 | 100 | 100 | 100 | 100 |
| VIII | 0 | 0 | 0 | 0 | 0 | 0 |
| IX | 100 | 100 | 100 | 100 | 100 | 100 |
| X | 0 | 0 | 0 | 0 | 0 | 0 |
| XI | 100 | 0 | 80 | 100 | 100 | 100 |
| XII | 100 | 0 | 50 | 40 | 80 | 0 |
| XIII | 100 | 100 | 100 | 100 | 100 | 100 |
| XIV | 0 | 0 | 0 | 0 | 70 | 30 |
| XV | 100 | 70 | 90 | 100 | 100 | 100 |
| XVI | 0 | 0 | 0 | 0 | 80 | 0 |

Table 2
Postemergence Herbicidal Activity of 3-(substituted amino(isothiazolylureas and -alkanamides (expressed as percent kill at 8.96 kg/hectare)

| Compound of Example | Lima Bean | Corn | Wild Oats | Lettuce | Mustard | Crabgrass |
|---|---|---|---|---|---|---|
| I | 100 | 0 | 90 | 100 | 100 | 100 |
| II | 100 | 30 | 100 | 100 | 100 | 100 |
| III | 100 | 100 | 100 | 100 | 100 | 100 |
| IV | 100 | 0 | 100 | 100 | 100 | 100 |
| V | 100 | 100 | 100 | 100 | 100 | 100 |
| VI | 50 | 0 | 30 | 100 | 40 | 50 |
| VII | 100 | 100 | 100 | 100 | 100 | 100 |
| VIII | 0 | 0 | 20 | 100 | 100 | 0 |
| IX | 100 | 100 | 100 | 100 | 100 | 100 |
| X | 30 | 0 | 0 | 50 | 30 | 30 |
| XI | 100 | 30 | 100 | 100 | 100 | 50 |
| XII | 100 | 30 | 100 | 100 | 100 | 30 |
| XIII | 100 | 100 | 100 | 100 | 100 | 100 |
| XIV | 75 | 0 | 20 | 70 | 100 | 80 |
| XV | 100 | 100 | 100 | 100 | 100 | 100 |
| XVI | 30 | 0 | 50 | 50 | 100 | 50 |

For herbicidal application, the compounds of this invention may be utilized in diverse formulations including the agricultural adjuvants and agricultural carriers, i.e. those materials normally employed to facilitate the dispersion of active ingredients in agricultural applications, recognizing the fact that the formulation and mode of application of a toxicant may affect the activity of the material in a given application. Thus, a compound of this invention may be formulated as a granule of relatively large particle size, as a wettable powder, as an emulsifiable concentrate, as a solution, or as any of several other known types of formulations, depending on the desired mode of application.

Granular formulations are particularly useful for aerial distribution or for penetration of a canopy of foliage. Useful granular formulations may be of several types. Impregnated granules are those wherein the active ingredient is applied to large particles of an absorbent carrier, such as an attapulgite or kaolin clay, corncobs, expanded mica, etc., normally in the form of a solution in a solvent. Surface-coated granules may be produced by spraying the molten active ingredient onto the surface of a generally nonabsorbent particle or by spraying on a solution of active ingredient in a solvent. The core may be water-soluble such as a prilled fertilizer, or insoluble such as sand, marble chips or coarse talc. Particularly useful is a granule wherein a wettable powder is applied as a surface coating to a sand or other insoluble particle such that the wettable powder may be dispersed on contact of the granule with moisture. Granules may be produced by agglomeration of dusts or powders by compaction rollers, by extrusion through a die or by use of a granulating disc. Granular formulations may vary widely in concentration, with useful formulations containing as little as 0.5% or as much as 95% of active ingredient.

Wettable powders, also useful formulations for both pre- and postemergence herbicides, are in the form of finely divided particles which disperse readily in water or other dispersants. The wettable powder is ultimately applied to the soil or to the undesired plant growth either as a finely divided dry material or as an emulsion in water or other liquid. Typical carriers for wettable powders include fuller's earth, kaolin clays, silicas and other highly absorbent, readily wet inorganic diluents. Wettable powders normally are prepared to contain about 5 to 80% of active ingredient, depending on the absorbency of the carrier, and usually also contain a small amount of a wetting, dispersing or emulsifying agent to facilitate dispersion. For example, a useful wettable powder formulation contains 80.8 parts of 1-methyl-3-(4-carbamoyl-3-(dimethylamino)-5-isothiazolyl)urea, 17.9 parts of palmetto clay, and 1.0 part of sodium lignosulfonate and 0.3 part of sulfonated aliphatic polyester as wetting agents.

Other useful formulations for herbicidal applications are the emulsifiable concentrates, which are homogeneous liquid or paste compositions dispersible in water or other dispersant, and may consist entirely of a compound of this invention with a liquid or solid emulsifying agent, or may also contain an agriculturally acceptable liquid carrier, such as xylene, heavy aromatic naphthas, isophorone and other nonvolatile organic solvents.

Typical wetting, dispersing or emulsifying agents used in agricultural formulations include, for example, the alkyl and alkylaryl sulfonates and sulfates and their sodium salts; polyethylene oxides; sulfonated oils, fatty acid esters of polyhydric alcohols; and other types of surface-active agents, many of which are available in commerce. The surface-active agent, when used, normally comprises from 1 to 15% by weight of the herbicidal composition.

These formulations may be applied without further dilution or as dilute solutions, emulsions or suspensions in water or other suitable diluent. The compositions may be applied to the area wherein control is desired by spraying onto the undesired vegetation or onto the surface of the soil in the case of liquid compositions or by distribution from mechanical equipment in the case of solids. The surface-applied material may also be blended into the upper layer of soil by cultivation, or left as applied, as is appropriate to gain the optimum results with the particular treatment.

The active herbicidal compounds of this invention may be formulated and/or applied with insecticides, fungicides, nematicides, plant-growth regulators, fertilizers, and other agricultural chemicals. In applying the active compounds of this invention, whether formulated alone or with other agricultural chemicals, an effective amount and concentration of isothiazolylurea are of course employed.

It is apparent that various modifications may be made in the formulation and application of the novel compounds of this invention, without departing from the inventive concept herein, as defined in the following claims:

I claim:
1. A substituted isothiazolylurea of the formula

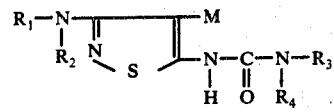

in which $R_1$ and $R_2$ are alkyl, or taken together form a tetramethylene radical; $R_3$ is alkyl; $R_4$ is alkyl or hydrogen; M is cyano or carbamoyl.

2. A compound of claim 1 in which M is cyano and $R_3$ and $R_4$ are both alkyl.

3. The compound of claim 2 which is 1,1-dimethyl-3-(4-cyano-3-(dimethylamino)-5-isothiazolyl)urea.

4. The compound of claim 2 which is 1,1-dimethyl-3-(4-cyano-3-(ethylmethylamino)-5-isothiazolyl)urea.

5. A compound of claim 1 in which M is carbamoyl and $R_4$ is hydrogen.

6. A compound of claim 5 in which $R_3$ is methyl.

7. The compound of claim 6 which is 1-methyl-3-(4-carbamoyl-3-(dimethylamino)-5-isothiazolyl)urea.

8. The compound of claim 6 which is 1-methyl-3-(4-carbamoyl-3-(diethylamino)-5-isothiazolyl)urea.

9. The compound of claim 6 which is 1-methyl-3-(4-carbamoyl-3-(dipropylamino)-5-isothiazolyl)urea.

10. The compound of claim 6 which is 1-methyl-3-(4-carbamoyl-3-(1-pyrrolidinyl)-5-isothiazolyl)urea.

11. The compound of claim 6 which is 1-methyl-3-(4-carbamoyl-3-(ethylmethylamino)-5-isothiazolyl)urea.

12. The compound of claim 6 which is 1-methyl-3-(3-(butylmethylamino)-4-carbamoyl-5-isothiazolyl)urea.

13. A compound of claim 1 in which M is cyano and $R_4$ is hydrogen.

14. The compound of claim 13 which is 1-methyl-3-(4-cyano-3-(dimethylamino)-5-isothiazolyl)urea.

15. The compound of claim 13 which is 1-methyl-3-(4-cyano-3-(ethylmethylamino)-5-isothiazolyl)urea.

16. An herbicidal composition comprising an herbicidally effective amount of a compound of claim 1 in admixture with an extender.

17. A method of preventing and destroying undesired plant growth which comprises applying to the locus to be protected an herbicidally effective amount of a compound of claim 1.

* * * * *

UNITED STATES PATENT AND TRADEMARK OFFICE
CERTIFICATE OF CORRECTION

PATENT NO. : 4,075,001
DATED : February 21, 1978
INVENTOR(S) : L. K. Gibbons

It is certified that error appears in the above—identified patent and that said Letters Patent is hereby corrected as shown below:

Column 3, line 38, "aqueous" should read --gaseous--. Column 4, line 66, "(4-cyano-3-(dimethylamino)-5-isothiazolyl-carbamate" should read --(4-cyano-3-(dimethylamino)-5-isothiazolyl)carbamate--.

Signed and Sealed this

Eighteenth Day of November 1980

[SEAL]

Attest:

SIDNEY A. DIAMOND

Attesting Officer

Commissioner of Patents and Trademarks